US 7,717,866 B2

(12) United States Patent
Damen

(10) Patent No.: US 7,717,866 B2
(45) Date of Patent: May 18, 2010

(54) PORTABLE DEVICE COMPRISING AN ACCELERATION SENSOR AND METHOD OF GENERATING INSTRUCTIONS OR ADVICE

(75) Inventor: Erik Petrus Nicolaas Damen, Zuidhorn (NL)

(73) Assignee: Move2Health Holding B.V., Doorwerth (NL)

( * ) Notice: Subject to any disclaimer, the term of this patent is extended or adjusted under 35 U.S.C. 154(b) by 574 days.

(21) Appl. No.: 10/477,165

(22) PCT Filed: May 6, 2002

(86) PCT No.: PCT/EP02/04968

§ 371 (c)(1),
(2), (4) Date: Jun. 25, 2004

(87) PCT Pub. No.: WO02/091923

PCT Pub. Date: Nov. 21, 2002

(65) Prior Publication Data
US 2004/0249315 A1 Dec. 9, 2004

(30) Foreign Application Priority Data
May 7, 2001 (EP) .................................. 01201653

(51) Int. Cl.
*A61B 5/103* (2006.01)
*A61B 5/117* (2006.01)
(52) U.S. Cl. ........................ 600/595; 702/131; 702/182; 702/183; 702/189
(58) Field of Classification Search ................. 600/595, 600/300–301; 702/131, 182–183, 189

See application file for complete search history.

(56) References Cited

U.S. PATENT DOCUMENTS

| 4,101,071 A | * | 7/1978 | Brejnik et al. ................. 377/49 |
| 4,855,942 A | * | 8/1989 | Bianco ........................ 702/160 |
| 4,911,427 A | * | 3/1990 | Matsumoto et al. ............ 482/9 |
| 4,951,197 A | | 8/1990 | Mellinger |
| 4,962,469 A | | 10/1990 | Ono et al. |
| 5,108,989 A | | 4/1992 | Amento et al. |
| 5,117,444 A | * | 5/1992 | Sutton et al. ................ 377/24.2 |
| 5,410,472 A | | 4/1995 | Anderson .............. 364/413.04 |

(Continued)

FOREIGN PATENT DOCUMENTS

DE 195 18 932 A1 11/1995

(Continued)

OTHER PUBLICATIONS

Diabetech, "News at Diabetech," http://www.diabetech.net, Aug. 27, 2004, 8 pages.

(Continued)

*Primary Examiner*—Max Hindenburg
*Assistant Examiner*—Rene Towa
(74) *Attorney, Agent, or Firm*—Patent Capital Group

(57) ABSTRACT

The invention pertains to a portable device comprising a housing, a display, a storage medium, at least one acceleration sensor, means for calculating an activity parameter based on the signal generated by the acceleration sensor, storing the calculated parameter in the storage medium, and showing the same in the display. The said parameter is the Physical Activity Index (PAI) or a derivative thereof.

12 Claims, 4 Drawing Sheets

U.S. PATENT DOCUMENTS

| | | | |
|---|---|---|---|
| 5,436,228 A | 7/1995 | Postlethwaite et al. | |
| 5,466,200 A | 11/1995 | Ulrich et al. | 482/4 |
| 5,474,090 A | 12/1995 | Begun et al. | 128/707 |
| 5,527,239 A | 6/1996 | Abbondanza | 482/8 |
| 5,573,013 A * | 11/1996 | Conlan | 600/595 |
| 5,593,431 A * | 1/1997 | Sheldon | 607/19 |
| 5,598,849 A | 2/1997 | Browne | 128/707 |
| 5,611,806 A | 3/1997 | Jang | |
| 5,649,968 A | 7/1997 | Alt et al. | |
| 5,702,323 A | 12/1997 | Poulton | 482/8 |
| 5,749,372 A | 5/1998 | Allen et al. | |
| 5,785,978 A | 7/1998 | Porter et al. | |
| 5,788,655 A * | 8/1998 | Yoshimura et al. | 600/587 |
| 5,807,283 A | 9/1998 | Ng | |
| 5,810,747 A | 9/1998 | Brundy et al. | 600/595 |
| 5,813,863 A | 9/1998 | Sloane et al. | |
| 5,885,231 A | 3/1999 | Cramer et al. | |
| 5,890,997 A | 4/1999 | Roth | 482/8 |
| 5,899,963 A | 5/1999 | Hutchings | |
| 5,916,063 A | 6/1999 | Alessandri | 482/4 |
| 5,919,149 A | 7/1999 | Allum | |
| 5,925,001 A | 7/1999 | Hoyt et al. | |
| 5,931,763 A | 8/1999 | Alessandri | 482/4 |
| 5,955,667 A | 9/1999 | Fyfe | |
| 5,964,729 A | 10/1999 | Choi et al. | |
| 5,967,789 A | 10/1999 | Segel et al. | |
| 5,973,618 A | 10/1999 | Ellis | |
| 5,976,083 A | 11/1999 | Richardson et al. | 600/300 |
| 5,989,200 A | 11/1999 | Yoshimura et al. | 600/587 |
| 6,021,351 A * | 2/2000 | Kadhiresan et al. | 607/19 |
| 6,030,404 A | 2/2000 | Lawson et al. | |
| 6,032,530 A | 3/2000 | Hock | |
| 6,039,688 A | 3/2000 | Douglas et al. | |
| 6,045,513 A * | 4/2000 | Stone et al. | 600/508 |
| 6,046,761 A | 4/2000 | Echerer | |
| 6,052,654 A | 4/2000 | Gaudet et al. | |
| 6,063,046 A | 5/2000 | Allum | |
| 6,065,138 A | 5/2000 | Gould et al. | |
| 6,080,106 A | 6/2000 | Lloyd et al. | |
| 6,095,991 A | 8/2000 | Krausman et al. | |
| 6,101,478 A | 8/2000 | Brown | |
| 6,122,340 A | 9/2000 | Darley et al. | |
| 6,135,951 A | 10/2000 | Richardson et al. | 600/300 |
| 6,145,389 A | 11/2000 | Ebeling et al. | |
| 6,151,586 A | 11/2000 | Brown | |
| 6,168,569 B1 | 1/2001 | McEwen et al. | |
| 6,206,829 B1 | 3/2001 | Lliff | |
| 6,229,454 B1 | 5/2001 | Heikkila et al. | |
| 6,240,393 B1 * | 5/2001 | Brown | 705/1 |
| 6,273,856 B1 | 8/2001 | Sun et al. | |
| 6,290,646 B1 | 9/2001 | Cosentino et al. | |
| 6,305,221 B1 * | 10/2001 | Hutchings | 73/488 |
| 6,356,856 B1 | 3/2002 | Damen et al. | |
| 6,377,179 B1 | 4/2002 | Fulton | |
| 6,454,705 B1 | 9/2002 | Cosentino et al. | |
| 6,473,483 B2 * | 10/2002 | Pyles | 377/24 |
| 6,478,736 B1 * | 11/2002 | Mault | 600/300 |
| 6,497,638 B1 | 12/2002 | Shea | 482/8 |
| 6,506,152 B1 | 1/2003 | Lackey et al. | |
| 6,513,532 B2 * | 2/2003 | Mault et al. | 600/595 |
| 6,516,749 B1 | 2/2003 | Salasidis | |
| 6,519,495 B1 * | 2/2003 | Sun et al. | 607/18 |
| 6,571,200 B1 * | 5/2003 | Mault | 702/182 |
| 6,578,291 B2 | 6/2003 | Hirsch et al. | |
| 6,582,380 B2 | 6/2003 | Kazlausky et al. | |
| 6,590,536 B1 | 7/2003 | Walton | |
| 6,604,419 B2 * | 8/2003 | Guzman | 73/491 |
| 6,605,038 B1 * | 8/2003 | Teller et al. | 600/300 |
| 6,605,044 B2 | 8/2003 | Bimbaum | |
| 6,626,799 B2 | 9/2003 | Watterson et al. | |
| 6,669,600 B2 | 12/2003 | Warner | |
| 6,692,436 B1 | 2/2004 | Bluth et al. | |
| 6,703,939 B2 | 3/2004 | Lehrman et al. | |
| 6,714,133 B2 | 3/2004 | Hum et al. | |
| 6,731,213 B1 | 5/2004 | Smith | |
| 6,790,178 B1 | 9/2004 | Mault | |
| 6,805,006 B2 | 10/2004 | Guzman | |
| 6,807,869 B2 | 10/2004 | Farringdon et al. | |
| 6,819,247 B2 | 11/2004 | Birnbach et al. | |
| 6,825,777 B2 | 11/2004 | Vock et al. | |
| 6,878,121 B2 | 4/2005 | Krausman et al. | |
| 6,989,550 B2 | 5/2005 | Blackadar et al. | |
| 6,918,858 B2 | 7/2005 | Watterson et al. | |
| 6,928,324 B2 * | 8/2005 | Park et al. | 607/20 |
| 6,997,852 B2 | 2/2006 | Watterson et al. | |
| 6,997,882 B1 | 2/2006 | Parker et al. | |
| 7,108,681 B2 | 9/2006 | Gartstein et al. | |
| 7,137,566 B2 | 11/2006 | Silverbrook et al. | |
| 7,156,289 B2 | 1/2007 | Silverbrook et al. | |
| 7,178,718 B2 | 2/2007 | Silverbrook et al. | |
| 7,181,448 B2 | 2/2007 | Silverbrook et al. | |
| 7,184,962 B2 | 2/2007 | Kalnas et al. | |
| 7,278,966 B2 | 10/2007 | Hjelt et al. | |
| 7,373,820 B1 | 5/2008 | James | |
| 7,502,255 B2 | 3/2009 | Li | |
| 7,559,877 B2 | 7/2009 | Parks et al. | |
| 7,603,255 B2 | 10/2009 | Case et al. | |
| 2001/0004234 A1 | 6/2001 | Petelenz et al. | |
| 2001/0047125 A1 | 11/2001 | Quy | |
| 2001/0048364 A1 | 12/2001 | Kalthoff et al. | |
| 2002/0013717 A1 | 1/2002 | Ando et al. | |
| 2002/0082906 A1 | 6/2002 | Kirshner | |
| 2002/0099356 A1 | 7/2002 | Unger et al. | |
| 2002/0109600 A1 | 8/2002 | Mault et al. | |
| 2003/0017848 A1 | 1/2003 | Engstrom et al. | |
| 2003/0050537 A1 | 3/2003 | Wessel | |
| 2003/0122677 A1 | 7/2003 | Kail | |
| 2003/0126593 A1 | 7/2003 | Mault | |
| 2003/0135391 A1 | 7/2003 | Edmundson et al. | |
| 2003/0199811 A1 | 10/2003 | Sage et al. | |
| 2003/0208110 A1 | 11/2003 | Mault | |
| 2004/0049251 A1 | 3/2004 | Knowlton | |
| 2004/0052750 A1 | 3/2004 | Lee et al. | |
| 2004/0087992 A1 | 5/2004 | Gartstein et al. | |
| 2004/0092367 A1 | 5/2004 | Corbalis et al. | |
| 2004/0111291 A1 | 6/2004 | Dust et al. | |
| 2004/0130446 A1 | 7/2004 | Chen et al. | |
| 2004/0132461 A1 | 7/2004 | Duncan | |
| 2004/0133455 A1 | 7/2004 | McMahon | |
| 2004/0247748 A1 | 12/2004 | Bronkema | |
| 2004/0260210 A1 | 12/2004 | Ella et al. | |
| 2005/0010439 A1 | 1/2005 | Short | |
| 2005/0107723 A1 | 5/2005 | Wehman et al. | |
| 2005/0137531 A1 | 6/2005 | Prausnitz et al. | |
| 2005/0202934 A1 | 9/2005 | Olrik et al. | |
| 2005/0209061 A1 | 9/2005 | Crawford et al. | |
| 2005/0225868 A1 | 10/2005 | Nelson et al. | |
| 2005/0228692 A1 | 10/2005 | Hodgdon | |
| 2005/0234742 A1 | 10/2005 | Hodgdon | |
| 2005/0245793 A1 | 11/2005 | Hilton et al. | |
| 2006/0025282 A1 | 2/2006 | Redmann | |
| 2006/0229163 A1 | 10/2006 | Waters | |
| 2006/0264730 A1 | 11/2006 | Stivoric et al. | |
| 2007/0073217 A1 | 3/2007 | James | |
| 2007/0135264 A1 | 6/2007 | Rosenberg | |
| 2007/0135690 A1 | 6/2007 | Nicholl | |
| 2007/0219059 A1 | 9/2007 | Schwartz et al. | |
| 2007/0260483 A1 | 11/2007 | Nurmela et al. | |
| 2008/0086325 A1 | 4/2008 | James | |
| 2008/0090703 A1 | 4/2008 | Rosenberg | |
| 2008/0096726 A1 | 4/2008 | Riley et al. | |
| 2008/0155077 A1 | 6/2008 | James et al. | |
| 2008/0176655 A1 | 7/2008 | James | |
| 2008/0182723 A1 | 7/2008 | Aaron et al. | |

| | | | |
|---|---|---|---|
| 2008/0258921 | A1 | 10/2008 | Woo et al. |
| 2008/0306762 | A1 | 12/2008 | James |
| 2008/0306763 | A1 | 12/2008 | James |
| 2009/0005220 | A1 | 1/2009 | Lee et al. |
| 2009/0048493 | A1 | 2/2009 | James et al. |
| 2009/0093341 | A1 | 4/2009 | James et al. |
| 2009/0171614 | A1 | 7/2009 | Damen |
| 2009/0204422 | A1 | 8/2009 | James |
| 2009/0216629 | A1 | 8/2009 | James |

FOREIGN PATENT DOCUMENTS

| | | |
|---|---|---|
| EP | 0797 169 A1 | 9/1996 |
| EP | 1 159 989 A1 | 5/2000 |
| EP | 1366712 | 12/2003 |
| WO | WO 96/29007 | 9/1996 |
| WO | WO 00/52604 | 9/2000 |
| WO | WO02/069803 | 9/2002 |
| WO | WO 02/091923 A1 | 11/2002 |
| WO | WO 03/089069 A1 | 10/2003 |
| WO | WO 2007/011788 | 1/2007 |

OTHER PUBLICATIONS

Horst Liebl, Co., "Confidential - Evaluation II - On the Needling-device Medical Roll-CIT," made by Environ, May 2001, 5 pages.
K. Anastassakis, M.D., Ph.D., "The Dermaroller Series," May 2005, 28 pages.
D.R. Owen, Ph.D., "Peptides, Oligopeptides, Lipopeptides and Polypeptides," Official Publication of the Society of Plastic Surgical Skin Care Specialists, Spring 2005, 2 pages.
"History of the Dermaroller," www.dermaroller.de/History.htm, printed approximately Jul. 2005, 7 pages.
DermaRoller™, http://www.dermaroller.de/derma_engl.htm, printed Jul. 11, 2005, 4 pages.
"The Dermaroller - A New and Highly Effective Procedure to Treat Acne-Scars by Micro-Needling," approx. 2005, 3 pages.
Horst Liebl, Co., "The Collagen-Induction-Therapy CIT with the CIT-Roller," approx. 2005, 3 pages.
DermaRolle™-MODELS, approx. 2005, 3 pages.
"The Dermaroller - An Effective Alternative for Scar-Therapies," approx. 2005, 5 pages.
"The Collagen-Induction-Therapy (CIT) with the DermaRolle™- The "soft" alternative for all common Laser & Peeling-Methods," approx. 2005, 5 pages.
Frequently Asked Questions (FAQs) About the DermarRoller™, approx. 2005, 4 pages.
Horst Liebl, Co., "Technical evaluation of the Roll-CIT," Manufactured by ENVIRON - South Africa, approx. 2005, 3 pages.
Horst Liebl, Co., "Technical Data & Description of the DermaRoller™," approx. 2005, 1 page.
Notification of Transmittal of the International Search Report and the Written Opinion of the International Searching Authority, or the Declaration for International Application No. PCT/US06/27502 mailed Mar. 19, 2007, 6 pages.
Clark, R.A.,"Biology of Dermal Wound Repair," Dermatologic Clinics, Oct. 1993, vol. 11, No. 4, pp. 647-666 (20 pages).
"Sport Brain First Step Pack," sportbrain.com (1 page) downloaded from http://www.sportbrain.com/Home/home.cfm?page=productsb_show&sk=c1235&us=99.95&cod= CL235 on Dec. 19, 2006.
"Nike + ipod Sport Kit," nike.com (1 page) downloaded from http://www.nike.com/index.ihtml#1=nikestore.home._pdp.cid-1/gid-118523/pid-118523&re=US&co=US&Ia=En on Dec. 19, 2006.
"What is the Bodybugg?," bodybugg.com (2 pages) downloaded from http://www.bodybugg.com/whatis.phpon Dec. 19, 2006.
"BioTrainer Weight Loss System,"Biotrainerusa.com (3 pages) dowloaded from http://www.biotrainerusa.com/learn2.asp on Dec. 19, 2006.
MSN Encarta - Definition of Accelerometer; date accessed: Nov. 19, 2007; http://encarta.msn.com/dictionary_1861583213/accelerometer.html; 2 pages.
Voicescape Absence Manager website with product description and information at http://absencemanager.voicescape.co.uk/sam/home/index.cfm, May 2008, 1 page.
"MySpace," myspace.com (2 pages) downloaded from http://www.myspace.com/, printed Jan. 16, 2007.
U.S. Appl. No. 10/819,730 filed Apr. 7, 2004, entitled "System and Method for Measuring an Economic Efficacy of an Intervention," Inventor(s) Richard W. Kersh, et al.
U.S. Appl. No. 10/915,916 filed Aug. 11, 2004, entitled "Process, System, and Method for Managing Healthcare Expenditures," Inventor(s) Terry L. James.
Raitio, Maarit. Caries risk determination and cost-effectiveness of targeted prevention in adolescents. Oulun yliopisto. Oulun University Library. 2002. Chapter 6.6. (3 pages) Printed Jun. 27, 2008 from http://Herkules.oulu.fi/. . .
U.S. Appl. No. 10/915,851 filed Aug. 11, 2004, entitled "System and Method for Designing an Intervention," Inventor(s) Terry L. James.
Jason, Leonard A., et al. Incentives and Competition in a Worksite Smoking Cessation Intervention. American Journal of Public Health. Feb. 1990. vol. 80, No. 2, p. 205 (3 pages).
Gaynor, Martin, et al. Physician Incentives in Health Maintenance Organizations. The Journal of Political Economy. Chicago: Aug. 2004. vol. 112, Iss. 4; p. 915 (17 pages).
U.S. Appl. No. 10/916,579 filed Aug. 11, 2004, entitled "System and Method for Implementing An Incentive Program To Encourage Participation in an Intervention," Inventor(s) Terry L. James.
U.S. Appl. No. 10/915,582 filed Aug. 11, 2004, entitled "System and Method for Population Health Management Data Collection and Communication," Inventor(s) Terry L. James.
"SportBrain Personal Fitness Assistant," sportbrain.com (1 page) downloaded from http://www.sportbrain.com/Home/Home.cfm, Jan. 16, 2007.
"NikePlus," nike.com (1 page) downloaded from http://www.nike.com/nikeplus, Jan. 16, 2007.
"Bodybugg Customized Calorie Management," bodybugg.com (2 pages) downloaded from http://www.bodybugg.com/fitnessresources.php, Jan. 16, 2007.
"BioTrainer Monitoring Programs," biotrainerusa.com (2 pages) downloaded from http://www.biotrainerusa.com/monitoring.asp, Jan. 16, 2007.
U.S. Appl. No. 12/098,539 filed Apr. 7, 2008, entitled "Accelerometer for Data Collection and Communication," Inventor(s): Terry L. James.
U.S. Appl. No. 12/176,369 filed Jul. 19, 2008, entitled "System and Method for Monitoring, Measuring, and Addressing Stress," Inventor(s): Terry L. James.

* cited by examiner

PORTABLE DEVICE COMPRISING AN ACCELERATION SENSOR AND METHOD OF GENERATING INSTRUCTIONS OR ADVICE

CROSS-REFERENCE TO RELATED APPLICATION

This Application is a Section 371 National Stage Application of International Application No. PCT/EP02/04968, filed May 6, 2002 and published as WO 02/091923 A1 on Nov. 21, 2002, published in English, which claims priority to EP Application No. 01201653.1, filed May 7, 2001.

BACKGROUND OF THE INVENTION

The invention pertains to a portable device comprising a housing, a display, a storage medium, at least one acceleration sensor, means for calculating an activity parameter based on the signal generated by the acceleration, sensor, storing the calculated parameter in the storage medium, and showing the same in the display. The invention further pertains to a method of generating instructions or advice on how to increase physical activity as well as to a computer program comprising program code means for performing all the steps of the said method.

An example of a device as described above is known from e.g. U.S. Pat. No. 5,788,655, which relates to an exercise amount measuring device. This particular device calculates and displays total consumed calories, a remaining target calorie value, and a life activity index, which is classified into e.g. one of three ranks (I 'light', II 'medium', and III 'a little heavy'). To calculate these parameters, gender, age, height, and weight should be inputted by means of switches on the device.

Similar devices are disclosed in U.S. Pat. No. 5,989,200 en European patent application EP 0 797 169 A1.

U.S. Pat. No. 6,135,951 and U.S. Pat. No. 5,976,083 disclose a pedometer comprising a accelerometer subsystem. This subsystem and a heart beat subsystem are sampled and a moving average of acceleration is computed at each sample time. This moving average serves as a baseline for describing the acceleration waveform of a locomotor step.

Nowadays, many people are aware of the importance of healthy nutrition and sufficient exercise, yet appear unable to accomplish the same.

It is an object of the present invention to provide a device which stimulates (daily) physical activity through relatively uncomplicated and user-friendly means.

To this end, the device according to the invention is characterised in accordance with claim 1.

To this end, the device according to the invention is characterized in that the said parameter is the Physical Activity Index (PAI) or a derivative thereof. It is preferred that the PAI or a derivative thereof is calculated by multiplying an average of a processed signal or samples of a signal of the acceleration sensor with at least one constant.

It was surprisingly found that the PAI can be established readily, because the relation between the PAI and a processed signal or samples of a signal of the acceleration sensor is substantially linear.

For instance, PAI can be established by subtracting an offset from the processed signals or sample and multiplying the result with a constant. Such a constant is preferably determined by measuring the oxygen consumption of several subjects. Personal data of a user, such as gender, age, height, and weight, need not be inputted thus further enabling straightforward construction and enhancing ease of use. Also, the PAI is universal in that e.g. a PAI of 1.5 indicates a sedentary lifestyle independent of personal data, i.e. for a woman in her early twenties and a middle-aged man alike. Thus, suitable instructions or advice on how to increase physical activity can be readily selected based on the measured PAI and competition between e.g. colleagues or family members is being provoked.

It is preferred that the device comprises an input/output connector which enables the transfer of at least some of the stored information to a computer that contains or is connected or connectable to an electronic database and/or an electronic algorithm.

The method of generating instructions or advice according to the invention involves electronically obtaining, from an individual, the Physical Activity Index (PAI) or a derivative thereof and selecting, based on this parameter, one or more instructions or advice components from a database. It is preferred that the said parameter is downloaded by a remote server system, which selects, based on this parameter, one or more instructions or advice components from a database and wherein the selected items or a processed version thereof are subsequently uploaded.

The invention further pertains to a computer program comprising program code means for performing all the steps of this method. The computer program product may of course comprise both modules intended for implementation on a remote service system, e.g. located at a service provider, and modules intended for implementation on a local processing unit, such as a personal computer and/or portable computer device of some sort.

The Physical Activity Index (PAI), sometimes also referred to as Physical Activity Level (PAL), can be established by dividing the Total Energy Expenditure (TEE), i.e. the amount of energy that is consumed by a person during a selected period of time, e.g. a day, by the Basal Metabolic Rate (BMR), i.e. the amount of energy that is consumed by a person lying still on a bed for the same period of time. Typically, the PAI has the value of 1.0 when the person is lying on a bed, 1.5 when the person leads a sedentary life and 2.0 when the person has an active lifestyle.

It is noted that the TEE is roughly equal to the sum of the Activity Induced Energy Expenditure (AEE), the BMR, and the Diet Induced Energy Expenditure (DIE). The latter is usually equal to approximately 10% of the TEE.

Both AEE and BMR are proportional to the body weight of an individual. When compared to a relatively heavyweight person, a relatively lightweight person will consumes less energy both when in rest (BMR) and while performing a certain physical activity (AEE). In other words, the ratio of TEE to BMR, i.e. the PAI, is substantially independent of body weight. In this respect, the PAI and its derivatives differ from indices derived directly from AEE, such as joule or calorie consumption or an index proportional to such consumption. The latter indices require individual data (gender, age, height, and weight), whereas the device according to the present invention does not require such data.

An example of a preferred derivative of the PAI is the ratio of AEE to BMR, preferably multiplied by 100.

BRIEF DESCRIPTION OF THE DRAWINGS

The invention will now be explained with reference to the drawings in which a preferred device and method according to the present invention are schematically depicted.

DETAILED DESCRIPTION OF THE PREFERRED EMBODIMENTS

Figure 1A:
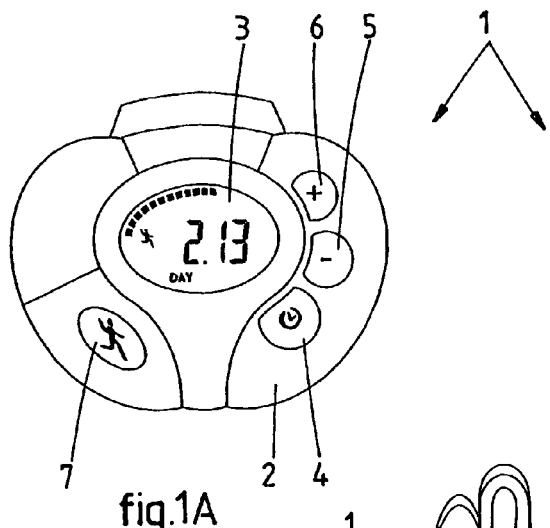
FIGS. 1A to 1C show respectively a front, rear and side view of a portable device according to the present invention.
Figure 1B:
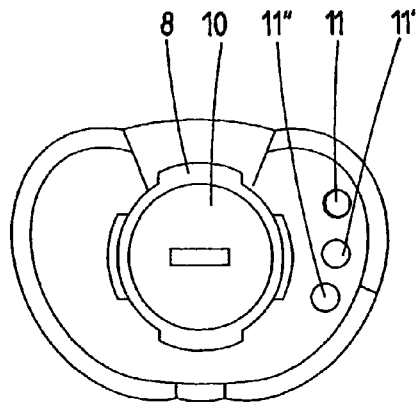
Figure 1C:
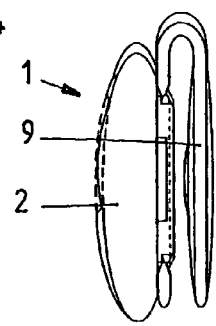
Figure 2A:
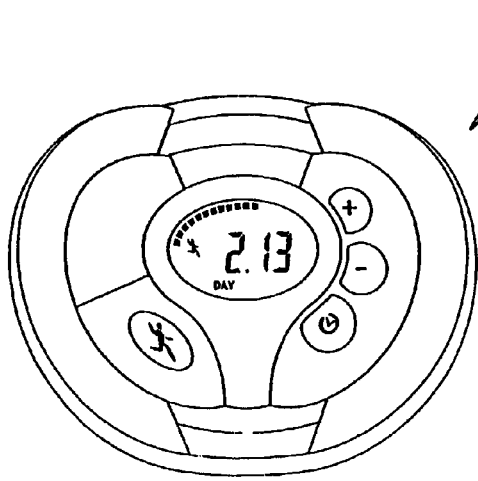
FIGS. 2A and 2B show a cradle for receiving the device according to FIG. 1B.
Figure 2B:
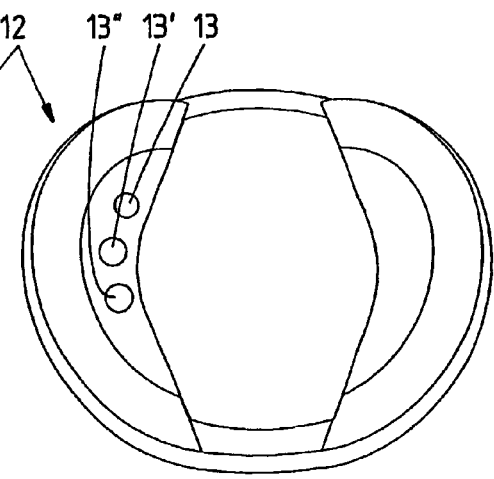

FIGS. 1A to 1C show an exemplary embodiment of the device according to the present invention, which embodiment will be referred to as activity monitor 1. The activity monitor 1 comprises a injection moulded housing 2 of a thermoplastic material such as PBT, a Liquid Crystal Display (LCD) 3, and four buttons 4 to 7. The rear side of the monitor comprises a bayonet catch 8 engaging a clip 9 for attaching the monitor 1 to an item of clothing and a cavity for accommodating a battery, which cavity is closed by means of a cover 10. It further comprises three I/O connectors, in this case butt contacts 11, 11', 11" which, upon placing the monitor in a complementary cradle, e.g. a docking station 12 shown in FIGS. 2A and 2B, contact three connectors 13, 13', 13" in the docking station 12 and enable the transfer of information, e.g. by means of an RS-232 protocol, between the monitor 1 and a computer to which the docking station 12 is connected.

The LCD 3 features the time, the numerical value of the Physical Activity Index (PAI) averaged over one or more selectable periods of time, and a segmented bar to graphically display the PAI within a specific range, e.g. from 1.0 to 3.0, in a number of discrete steps, e.g. of 0.1.

Instead of PAI, derivatives of PAI, such as (PAI−1)×100 or, if the Diet Induced Energy Expenditure (DIE) is to be excluded, (0,9×PAI−1)×100, can be employed. When using these particular derivatives, a value of 0 means that the user has been at rest (at least for the selected period of time for establishing PAI), whereas a value of e.g. 100 respectively 90 indicates an active lifestyle.

Buttons 4 to 7 serve to display and adjust time (respectively button 4 and buttons 5/6) and switch between displaying the PAI over e.g. the last day and the last week (button 7).

Figure 3:
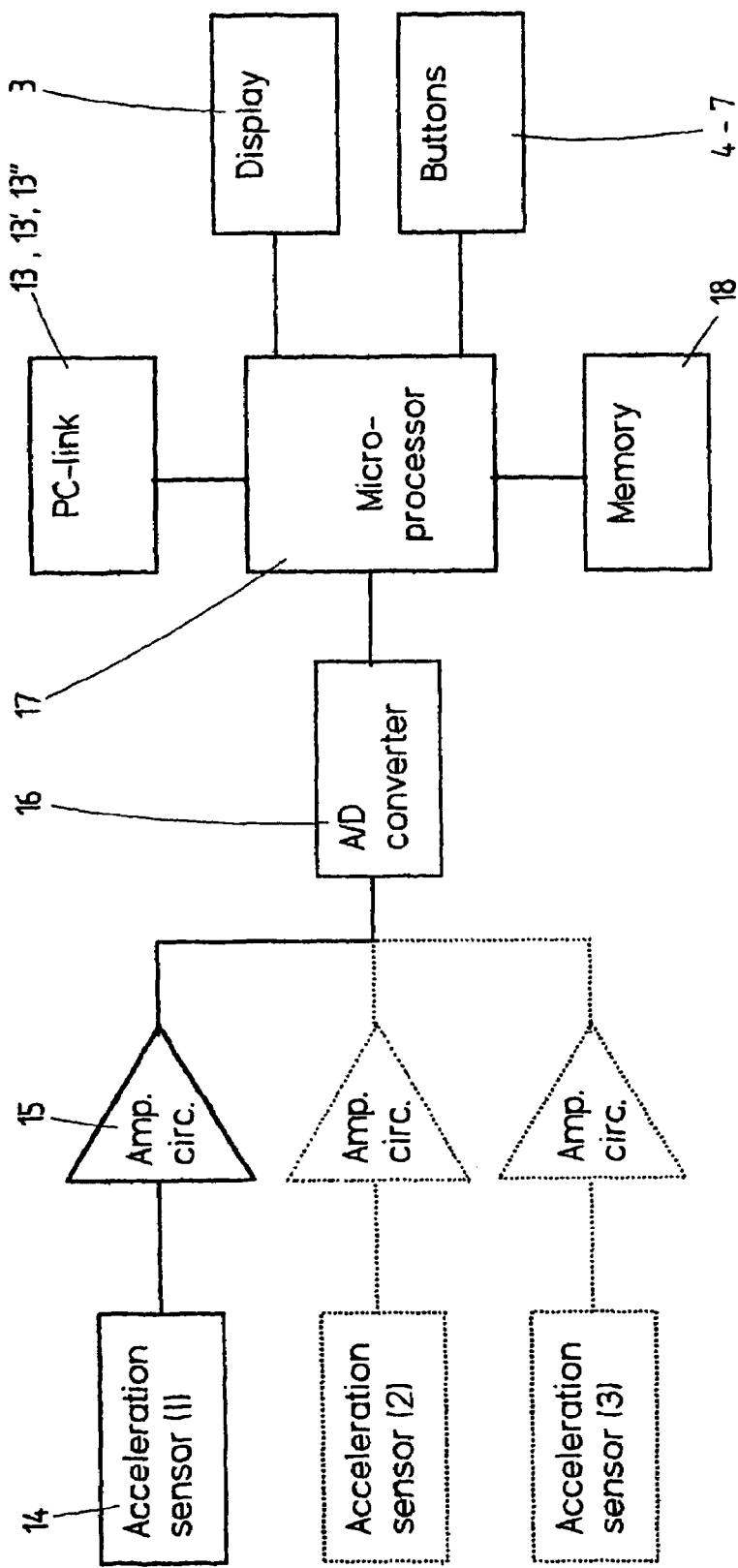
FIG. 3 is a block diagram of electrical circuitry for use in the device according the invention.

FIG. 3 shows a block diagram of an electrical circuitry for use in the activity monitor 1. The circuitry in this example comprises a single one-dimensional accelerometer 14, e.g. a so-called uniaxial piezo-electric accelerometer, which registers body movement of a wearer of the monitor 1 in the longitudinal direction or the antero-posterior and longitudinal directions. To achieve the latter, the accelerometer 14 is positioned at an angle of approximately 45 degrees to a horizontal position (as shown in FIGS. 1A and 1B) of the monitor 1. The aforementioned clip 9 in FIG. 1C facilitates attachment of the monitor 1 to e.g. the belt of a wearer in such a way as to ensure a substantially horizontal position during most of the time, especially when the wearer is standing upright. As a matter of course, it is also possible to employ e.g. three sensors 14 (as depicted by dotted lines).

The accelerometer 14 generates, dependent on the movements of a wearer, which typically occur in a frequency range from 0.5 to 16 Hz and with an amplitude of less than 5G, an analogous signal, e.g. a voltage fluctuating in a range from 0 mV to 10 mV. This signal is subsequently amplified by means of amplification circuitry 15 and converted to a digital sequence of numbers by means of an A/D converter 16 with a sample frequency of e.g. 32 Hz. A dedicated microprocessor 17 calculates the average of the absolute value of the acceleration data over e.g. the last day and the last week. To obtain the PAI the average is multiplied by a metabolic factor reflecting the average oxygen consumption of relatively large number of experimental subjects and a sensor calibration factor.

Thus, to calculate the average value of the PAI over a certain period of time, e.g. a day, the signal can be processed e.g. as follows. The absolute value of the signal, which fluctuates within the said range of from 0 mV to 10 mV, is amplified by an amplification factor and sampled by the A/D converter 16, which then generates a sample value e.g. an integer in a range from 0 to 255. Subsequently, the average of the sample values is calculated and multiplied by a metabolic factor, which can be established by comparing the said running average with true PAI values obtained by measuring oxygen consumption in one or more subjects in a manner which is known in itself. It is further preferred to employ a calibration factor to compensate for variations specific to the sensor in hand. For piezo-electric sensors variations were found to be ±20% and, accordingly, the calibration factor is preferably in a range from 0.8 to 1.2.

The microprocessor 17 stores the calculated PAIs in a memory 18, such as a random access memory chip, and shows the information, selected by the wearer by means of the appropriate button 4, in the display 3.

Figure 4:
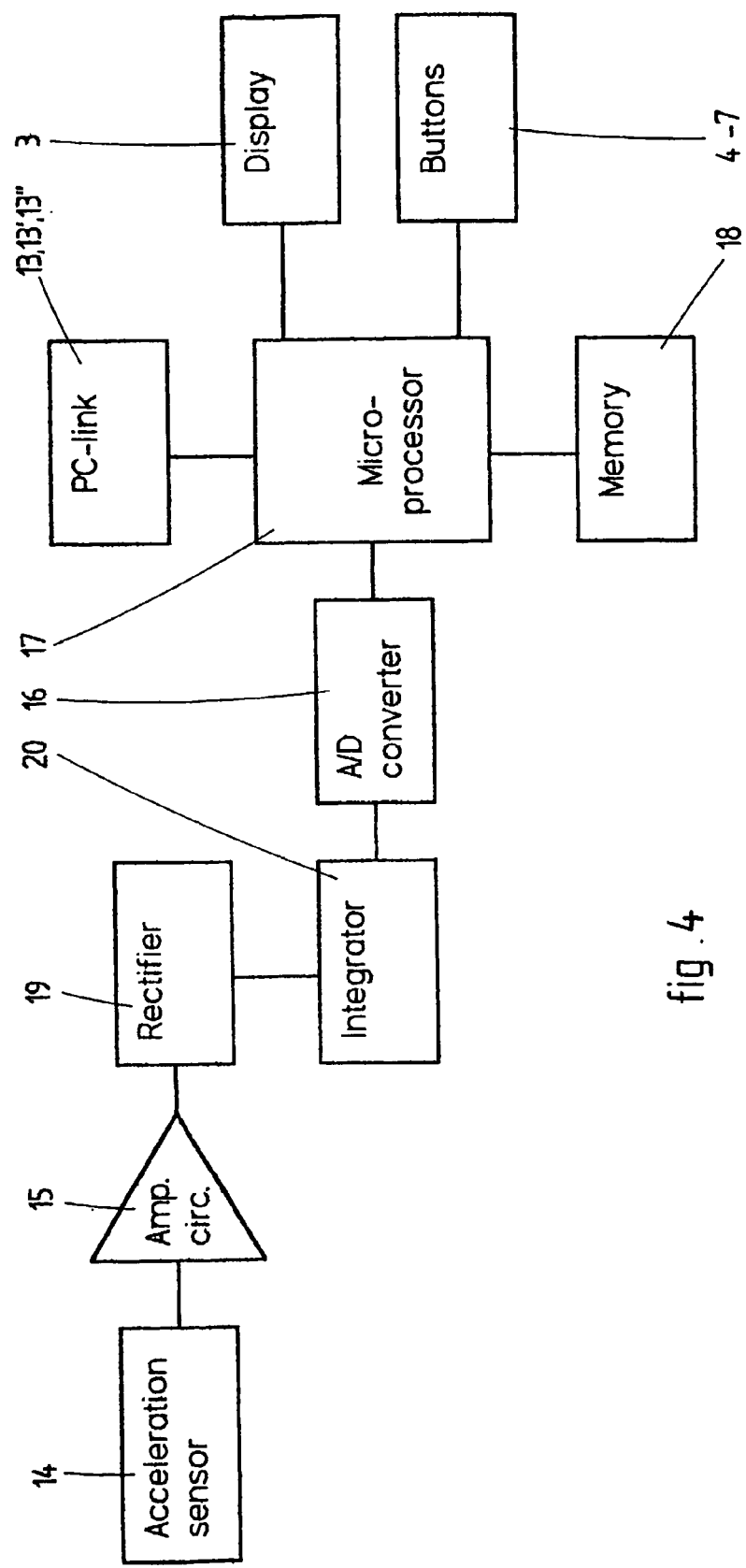
FIG. 4 is a block diagram of exemplary electrical circuitry for use in the device according to the invention.

FIG. 4 comprises an advantageous embodiment, wherein the circuitry comprises a rectifier 19 which comprises four diodes and an operational amplifier and is connected to the output of the amplifier 15. An integrator 20, which comprises a capacitor circuit, is connected to the output of the rectifier 19 and accumulates the analogous signal from the same. Instead of sampling the acceleration at a relatively high rate of e.g. 32 Hz, one can now reduce this rate to e.g. 1 Hz and, accordingly, significantly lower the power consumption of the activity monitor 1 and extend battery-life. A further advantage resides in that the PAI can be established with a high accuracy even when an low accuracy A/D converter (e.g. 8 bits) is being used.

Although the activity monitor 1 can be used as a stand-alone entity, which provides its user with accurate information of his or her activity, either relative to past activity of the user himself or relative to that of other people e.g. by means of the table or chart reflecting typical PAIs for specific persons (in terms of e.g. profession, sport, age, gender etc.), it is preferably used in conjunction with a personal computer (PC) and/or a remote computer, e.g. a server system. In that case, the user can compare his or her PAI with that of numerous other users and automatically select instructions or advice components from a database or calculate a new PAI goal by means of an algorithm.

To this end, the docking station 12 is connected to a PC or a remote server system in which software has been installed which preferably recognises the presence of the activity monitor in a known manner and performs a number of actions, e.g. download a 32-bit unique identification code, download last docking date, download PAI values of e.g. the last months, synchronise the clock of the activity monitor 1 and that of the PC or server system, and upload the present docking date.

Figure 5:
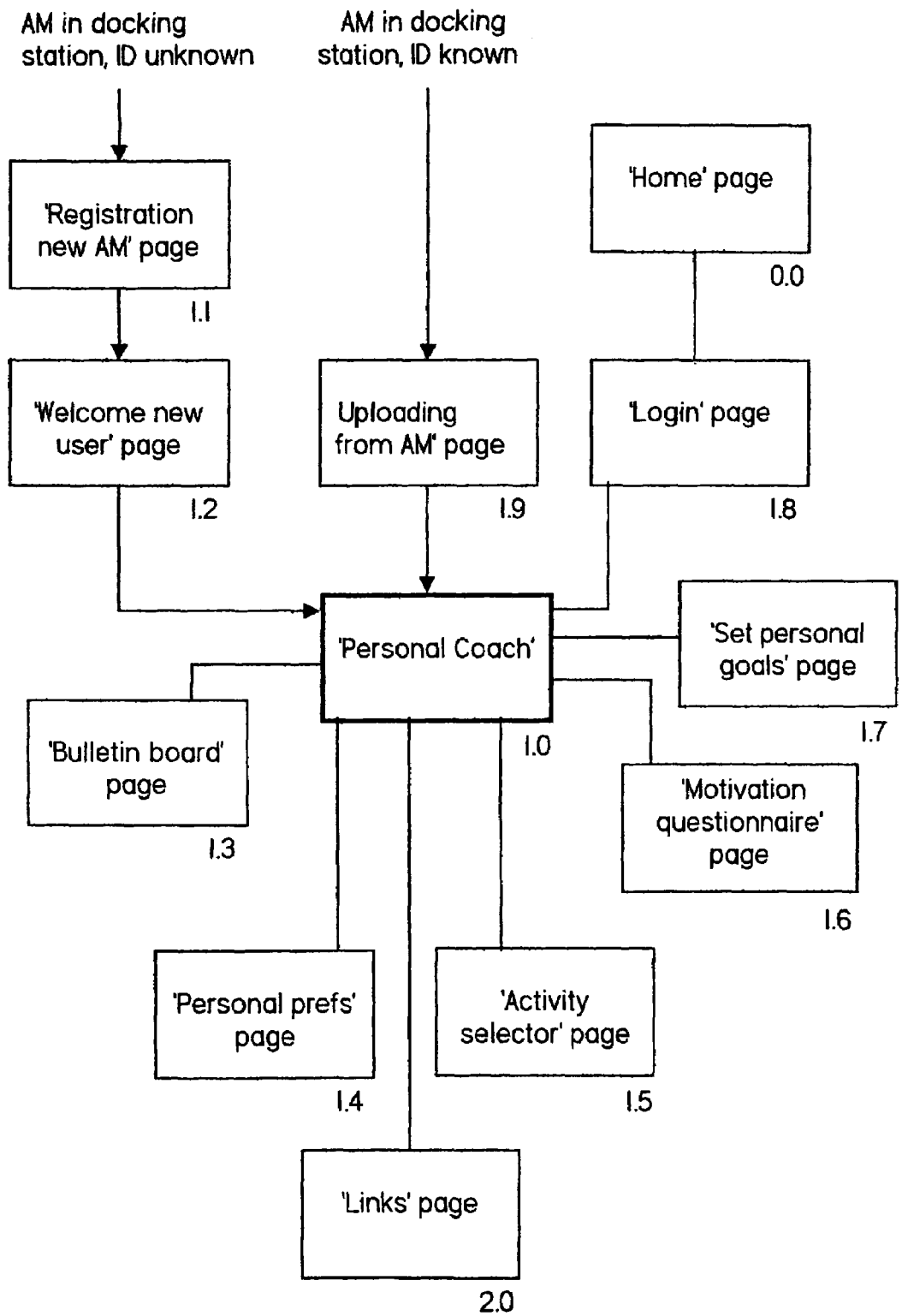
FIG. 5 is a flowchart of a website where the method according to the invention has been implemented.

A flowchart of a preferred website, which is installed on the said server system and which can be accessed via the Internet by the user with a web browser, such as Microsoft Explorer or Netscape Navigator or similar (future) means, is depicted in FIG. 5 and comprises a home page 0.0. This home page 0.0 shows several menus, which provide access to subpages of the website concerning, inter alia, the host, products of the host, health issues, registration, and login. The remainder of the home page 0.0 may comprise news items, advertisements, pictures, and the like.

A personal coach page 1.0 forms the kernel of the website. This page 1.0 can be accessed via a registration page 1.1 or login pages 1.8 and 1.9. The former page 1.1 comprises an electronic form for gathering information from users of the activity monitor 1 who visit the website for the first time. Such information may comprise the name, address, city, country, weight, height, age, gender, and weight goal, and will be used by the personal coach page 1.0 to generate instructions and personalised advice. The registration page 1.1 further provides a username and password, which enables users to by-pass registration page 1.1 and enter the personal coach page 1.0 directly through login pages 1.8 and 1.9, and links the username information to the aforementioned unique address code. During login, the system compares the downloaded ID to the ID in the server so as to provided automatic login. The last docking date and most recent PAI values are used to update the database.

The personal goals of a user of the activity monitor 1 in terms of a desired activity level and a desired weight are calculated on a personal goals page 1.7. Such calculations can be based on the personal data of the customer, e.g., weight, height, age, and gender, as well as on other personal parameters that can be changed and/or updated on a preferences page 1.4 and/or on the average PAI of the first week and/or a numerical parameter representing the motivation of the customer and determined by means if a questionnaire page 1.6. Upon approval of the user, the calculated goals are set to be reached at the end of a coaching period of e.g. six months. During this period, the personal coach page 1.0 provides information concerning the personal history of the user in terms of activity and body weight and advice comprising suggestions on a preferred PAI selected on selector page 1.5 and activities required to reach the set personal goals, e.g. half an hour of walking every day or 5 km running every day.

Finally, the website comprises a links page 2.0 containing links to interesting pages that can help reach the personal goals, such a as a link to go to a page containing recipes which support a healthy lifestyle, a link to a service providing direct access to an instructor or dietician, and a link containing information on regional activities. If a goal is reached, the personal coach page 1.0 may start another page, which shows a message congratulating the user or sends an actual congratulations post card to the users' address. A special printer on the system could do this automatically.

The invention is not restricted to the above described embodiments which can be varied in a number of ways within the scope of the claims. For instance, the display device can be equipped with a rechargeable battery or even means for generating energy, such as a (piezo)electric generator which converts movement into electrical energy.

The invention claimed is:

1. A portable device comprising:
   a housing;
   a display;
   a storage medium;
   at least one acceleration sensor; and
   means arranged for calculating an activity parameter based on a signal generated by the at least one acceleration sensor, storing the calculated parameter in the storage medium, and showing the same in the display, wherein said parameter is the Physical Activity Index (PAI) or a derivative thereof, which is solely calculated by multiplying an average of the absolute values of a signal or samples of a signal of the at least one acceleration sensor with at least one constant, which at least one constant is independent of personal data of a user of the portable device, whereby the at least one constant is a universal metric that is not related to age, weight, or gender, the portable device being immediately operable after being powered ON such that the user that uses the portable device is not required to calibrate the portable device nor input his personal data to allow the portable device to accurately function.

2. The portable device according to claim 1, wherein the said average is at least multiplied by a calibration factor which depends on the sensor.

3. The portable device according to claim 1, wherein the device further comprises a rectifier for rectifying the signal generated by the acceleration sensor and a capacitor which is charged by the rectified signal.

4. The portable device according to claim 1, wherein the device comprises an input/output connector which enables transfer of at least some information stored on the storage medium to a computer connectable to at least one of an electronic database and an electronic algorithm.

5. The portable device according to claim 1, wherein the device comprises a clip for attaching the device to an item of clothing of a wearer such that rotation of the device with respect to the wearer is substantially avoided and wherein the sensor is adapted to be positioned at an angle in a range from 30 to 60 degrees to horizontal when the wearer is standing upright.

6. A method of generating instructions or advice on how to increase physical activity and tailored to at least one of objective needs and preferences of an individual, which method comprises:
   electronically obtaining a parameter concerning that individual using a portable device containing an acceleration sensor,
   wherein the said parameter is the Physical Activity Index (PAI) or a derivative thereof, which is solely calculated by multiplying an average of the absolute values of a signal or samples of a signal of the acceleration sensor with at least one constant, which constant is independent of personal data of a user of the portable device;
   electronically obtaining personal information of the individual for setting a personal goal of the individual;
   selecting, based on the obtained Physical Activity Index and the personal goal, one or more instructions or advice components from a database to reach said personal goal;
   accessing said instructions or advice components for use by the individual, whereby the at least one constant is a universal metric that is not related to age, weight, or gender, the portable device being immediately operable after being powered ON such that the user that uses the portable device is not required to calibrate the portable device nor input his personal data to allow the portable device to accurately function.

7. The method according to claim 6, and further comprising:
   uploading the said parameter to a remote server system, which performs the step of selecting; and
   downloading from the remote computer the selected one or more instructions or advice components or a processed version thereof.

8. The method according to claim 7, and further comprising uploading an identification code to the remote server system.

9. A computer program product code means stored in a computer readable medium for performing the following steps when said program product is run on a computer:

electronically obtaining a parameter concerning that individual; and selecting, based on the said parameter, one or more instructions or advice components from a database, wherein the said parameter is the Physical Activity Index (PAI) or a derivative thereof, which is solely calculated by multiplying an average of the absolute values of a signal or samples of a signal of an acceleration sensor with at least one constant, which constant is independent of personal data of a user of an portable device, whereby the at least one constant is a universal metric that is not related to age, weight, or gender, the portable device being immediately operable after being powered ON such that the user that uses the portable device is not required to calibrate the portable device nor input his personal data to allow the portable device to accurately function.

10. The computer program product code means of claim 9, and further comprising:

uploading the said parameter to a remote server system, which performs the step of selecting; and downloading from the remote computer the selected one or more instructions or advice components or a processed version thereof.

11. The computer program product code means of claim 10, and further comprising uploading an identification code to the remote server system.

12. A plurality of portable devices according to claim 1, wherein each of the plurality of portable devices wherein the means arranged for calculating the activity parameter includes said at least one constant such that for a plurality of different individuals, the calculated parameter will solely be calculated independent of personal data for the plurality of different individuals such that the individuals need not provide personal data for display of the activity parameter on the portable device associated with the individual.

* * * * *

UNITED STATES PATENT AND TRADEMARK OFFICE
CERTIFICATE OF CORRECTION

PATENT NO. : 7,717,866 B2
APPLICATION NO. : 10/477165
DATED : May 18, 2010
INVENTOR(S) : Erik Petrus Nicolaas Damen It is certified that error appears in the above-identified patent and that said Letters Patent is hereby corrected as shown below:

On the title page item "(73) Assignee:" Delete "Move2Health Holding B.V. Doorwerth (NL)" and insert -- Kersh Risk Management, Inc., Plano, TX (US) --.

Signed and Sealed this
Twenty-first Day of June, 2016

Michelle K. Lee
*Director of the United States Patent and Trademark Office*